Figure 1:
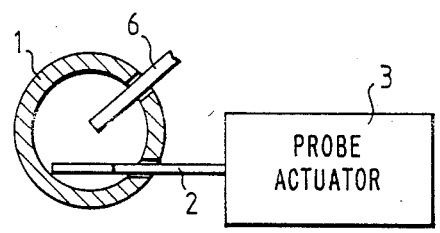

United States Patent [19]

Littlejohn et al.

[11] Patent Number: 4,824,241
[45] Date of Patent: Apr. 25, 1989

[54] ATOMIC SPECTROSCOPY

[75] Inventors: David Littlejohn; John Marshall, both of Glasgow, United Kingdom

[73] Assignee: U.S. Philips Corporation, New York, N.Y.

[21] Appl. No.: 57,727

[22] Filed: Jun. 2, 1987

Related U.S. Application Data

[63] Continuation of Ser. No. 581,484, Feb. 17, 1984, abandoned.

[30] Foreign Application Priority Data

Mar. 2, 1983 [GB] United Kingdom ............... 8305745

[51] Int. Cl.$^4$ ............................................. G01N 21/74
[52] U.S. Cl. ..................................... 356/36; 356/312; 356/244
[58] Field of Search ........................ 356/36, 312, 244

[56] References Cited

U.S. PATENT DOCUMENTS 4,406,540 9/1983 Grossman et al. ............... 356/312
4,443,105 4/1984 Huber et al. ..................... 356/312

FOREIGN PATENT DOCUMENTS 2052788 1/1981 United Kingdom ............... 356/312

OTHER PUBLICATIONS

Giri et al., *The Analyst*, vol. 108, No. 1283, Feb. 1983, pp. 244-253.
Manning et al., *Analytical Chemistry*, vol. 51, No. 14, Dec. 1979, pp. 2375-2378.

*Primary Examiner*—F. L. Evans
*Attorney, Agent, or Firm*—Paul R. Miller

[57] ABSTRACT

A method of atomic spectroscopy is provided involving the steps of inserting a probe into a cuvette, depositing a sample to be atomized onto the probe by means of a sample dispenser, withdrawing the probe from the cuvette, heating the cuvette to a desired temperature sufficient to atomize the sample, and then reinserting the probe into the cuvette. The sample dispenser may be a manually-operated pipette, or the dosing tube of an autosampler. Liquid samples may be dried by heating the cuvette to a temperature lower than the atomization temperature before withdrawing the probe from the cuvette. Both solid and liquid samples may be atomized by this procedure. Such samples also may be ashed where appropriate by heating the cuvette to a second temperature between the first temperature and the atomization temperature before withdrawing the probe from the cuvette. A spectrophotometer using the technique is also described.

8 Claims, 4 Drawing Sheets

ATOMIC SPECTROSCOPY

This is a continuation of application Ser. No. 581,484, filed Feb. 17, 1984, now abandoned.

The invention relates to a method of atomising a sample for atomic spectroscopy and to a spectrophotometer comprising an electrothermal atomiser in the form of a tubular body of electrically conductive material, means for depositing a sample on a probe, means for inserting the probe into the tubular body and means for passing an electrical current through the tubular body to heat the interior of the tubular body to a temperature which is sufficient to atomise the sample.

In U.K. Patent Application No. 2071845A a sample is introduced into a graphite tube atomiser by means of a sample carrier in the form of a wire helix of temperature-resistant, electrically conducting material, such as tungsten. The sample carrier is provided with electrical connections whereby it can be heated in a controlled manner by passing an electric current therethrough. Thus, in use when a liquid sample has been applied to the carrier, the sample can be dried and thermally decomposed externally of the graphite tube by heating the sample carrier. The sample carrier itself acts as a resistor in combination with the electrical connections and the power source, thus constituting a heating device.

This arrangement has some drawbacks. For example, only relatively small liquid sample quantities can be applied to the wire helix. In addition, the use of solid or powdery samples is not possible. Furthermore, the sample is essentially heated in a nonuniform way since the heating occurs first at the physical contact interface of the sample liquid and wire helix. Thus, the risk of sputtering of sample liquid is always present. Furthermore, the useful life of the heated wire helix is reduced because carbide formation occurs at its surface.

In other prior processes, a sample is sometimes introduced into a graphite crucible and inserted into a graphite tube wherein it is heated in a manner which is independent of the graphite tube. The independent heating of the crucible inside the graphite tube entails some of the disadvantages mentioned in U.K. Application No. 2071845A referred to above.

U.K. Patent Application No. 2088582A discloses sample introduction apparatus comprising a sample carrier for insertion into the graphite tube and shaped to accept non-gaseous sample material and means external to the graphite tube for radiantly heating the carrier. This enables the handling of relatively large solid or liquid sample quantities, including powdery material, without the disadvantages referred to above.

However, this arrangement entails the provision of extra elements such as the second heat source, thus increasing the cost and reducing the reliability of the apparatus.

It is an object of the invention to provide an alternative sample introduction apparatus for atomic spectroscopy.

The invention provides a method for atomising a sample for atomic spectroscopy comprising the steps of inserting a probe into a cuvette, depositing the sample to be atomised onto the probe, withdrawing the probe from the cuvette, heating the cuvette to a desired temperature sufficient to atomise the sample and inserting the probe into the cuvette.

This method gives the advantage that since the sample is deposited on the probe within the cuvette, a standard autosampler which has been designed to deposit the sample into the cuvette can be used.

When the method is used with samples in liquid form, it may include the step of drying the deposited sample by heating the cuvette to a desired temperature below the atomisation temperature before withdrawing the probe from the cuvette. This has the further advantage of enabling the second heat source to be dispensed with. It is conventional to provide a control means for raising the temperature of the cuvette to the atomisation temperature, which differs for different elements, and to monitor the temperature of the cuvette. This control means which is already present can be used to regulate the drying process as is conventional when the sample is deposited directly on the surface of the cuvette. The only differences between the requirements for the direct deposition and deposition onto the probe lie in the respective temperatures and times required to complete the drying process. These temperatures and times may be determined empirically for different samples.

The method may include the step of raising the temperature of the cuvette to a second higher-temperature to ash the sample after the sample has been dried with the second temperature being below the atomisation temperature. This step is necessary when samples which form a carbonaceous mass on drying, such as blood, are to be analysed. The second temperature and the time during which it is held are again determined empirically as is the case when the samples are deposited directly on the surface of the cuvette.

The invention further provides a spectrophotometer as described in the opening paragraph characterised in that the means for depositing the sample on the probe is arranged to deposit the sample on the probe when the probe is within the tubular body and in that means are provided for withdrawing the probe from the tubular body before the temperature of the interior of the body is raised to the atomisation temperature and for re-inserting the probe and sample into the tubular body after its interior temperature has reached the atomisation temperature.

This apparatus has the advantage that an autosampler can be used to deposit the sample either directly onto the surface of the tubular body or cuvette or onto the probe without requiring any modification. Thus a standard atomiser can be converted to a probe atomiser merely by providing an access aperture for the probe into the cuvette and the probe and actuator assembly.

Means may be provided for drying a liquid sample deposited on the probe before withdrawing the probe from the tubular body with the drying means comprising means for raising the temperature of the tubular body to a desired temperature below the atomisation temperature. By using the tubular body as the heating means for drying the sample, the necessity for a second heat source is eliminated, thus simplifying the apparatus.

Further means may be provided for ashing the sample before withdrawing the probe from the tubular body with the ashing means comprising means for raising the temperature of the tubular body to a second higher desired temperature, which second temperature is below the atomisation temperature. Again by using the tubular body to ash the sample, the necessity for a second heat source is eliminated. In conventional atomisers in which the sample is deposited on the inside wall of the tubular body, the sample has to be dried and ashed and therefore a controller which passes appropriate electrical currents through the tubular body for appropriate periods of time is conventionally provided. The controller is provided with means for selecting the temperature and the time for which the temperature is to be held with these means normally being a keyboard, and with a control loop which senses the actual temperature of the tubular body and regulates the voltage applied to produce the desired temperature. Alternatively the applied voltage may be selected and held at a constant value.

The means for withdrawing the probe from and inserting the probe in the tubular body may comprise a solenoid. This provides a convenient and inexpensive means for moving the probe from a first position within the tubular body to a second position external to the tubular body.

The tubular body may be constructed totally of pyrolytic graphite. The probe may also be constructed totally of pyrolytic graphite. Using pyrolytic graphite for the tubular body gives the advantages of long life and reduced permeation of the sample into the wall of the tubular body. If other forms of carbon are used for the tubular body, the life of the tubular body is significantly reduced because the region around the slot for the introduction of the probe and between the slot and the sample insertion aperture disintegrates after comparatively few atomisation cycles.

Figure 2:
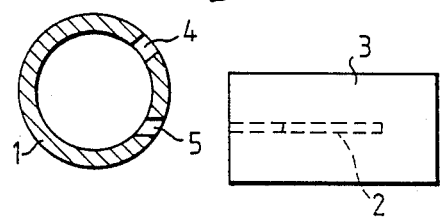
Figure 3:
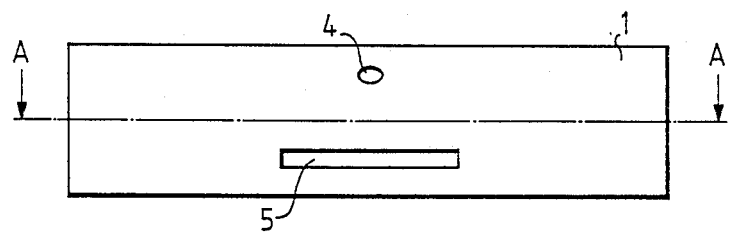
Figure 4:
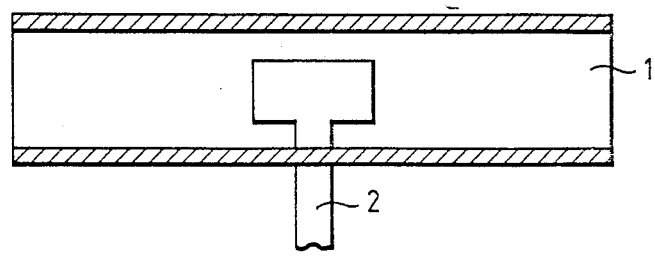
Figure 5:
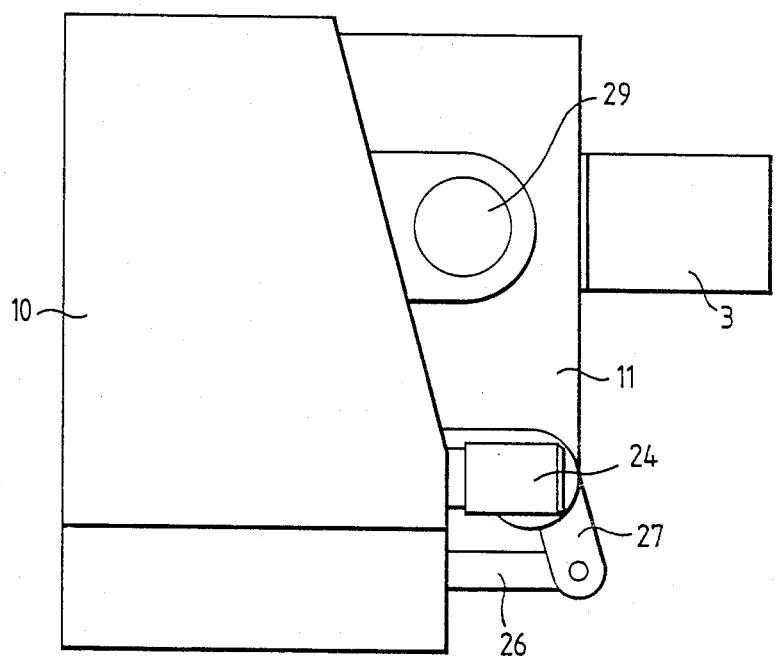
Figure 6:
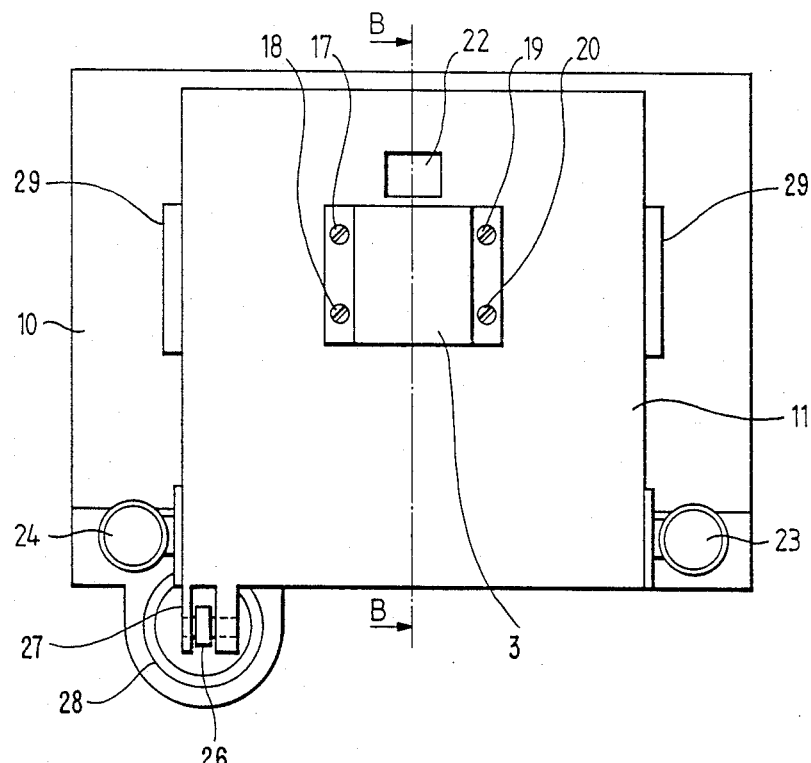
Figure 7:
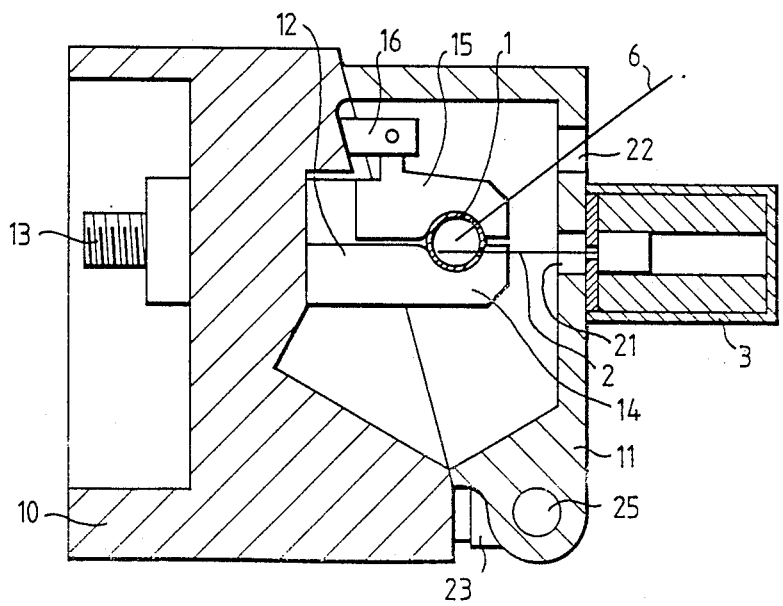
Figure 8:
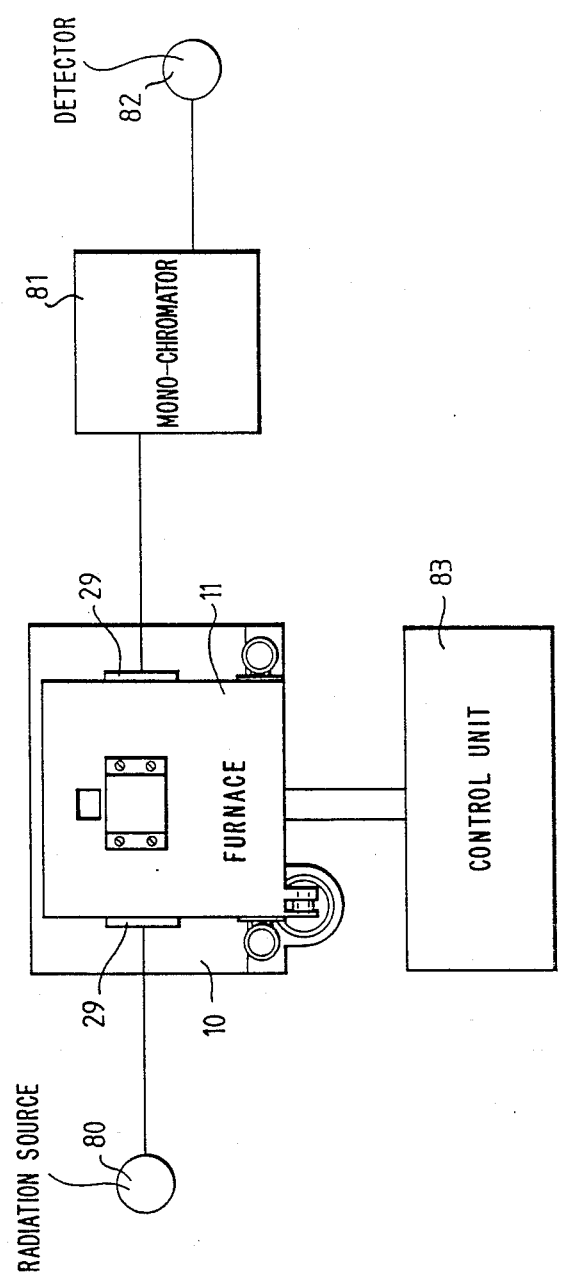

Embodiments of the invention will now be described, by way of example, with reference to the accompanying drawings, in which:

FIG. 1 is a sectional view of a cuvette, a probe within the cuvette and a sample deposition means for use in the method according to the invention, FIG. 2 shows the cuvette with the probe withdrawn therefrom, FIG. 3 shows a longitudinal elevation of the cuvette, FIG. 4 is a sectional view taken along line A—A of FIG. 3, FIG. 5 is a side elevation of a furnace for an atomic absorption spectrophotometer with the furnace being arranged to operate with the cuvette and probe assembly shown in FIGS. 1 to 4, FIG. 6 is a front elevation of the furnace shown in FIG. 5, FIG. 7 is a sectional view taken along line B—B of FIG. 6, and FIG. 8 is a diagrammatic schematic drawing of an atomic absorption spectrophotometer according to the invention.

FIGS. 1 and 2 show a graphite cuvette 1, a graphite probe 2 and a probe actuator 3. As can be seen from FIG. 3 in conjunction with FIGS. 1 and 2, the cuvette 1 is in the form of a hollow cylinder and is provided with a circular aperture 4 and a longitudinally extending slot 5. The probe actuator 3, which may conveniently be a solenoid, is arranged to be capable of moving the probe 2 between a first position within the cuvette, as shown in FIG. 1, and a second position outside the cuvette, as shown in FIG. 2. A sample dispenser 6 may be introduced into the cuvette 1 through the aperture 4 to enable a sample to be deposited on the probe 2 within the cuvette 1. The sample dispenser 6 may be a pipette manually introduced by an analyst or may be the dosing tube of an autosampler, such as the autosampler described in U.K. Patent Application No. 2049179A, the contents of which are incorporated by reference herein. FIG. 4 is a cross-sectional view on line A—A of FIG. 3 and shows the probe 2 in the first position within the cuvette 1.

In a method of atomising a sample using the arrangement shown in FIGS. 1 to 4, the probe 2 is introduced into the cuvette 1 by the actuator 3 and a sample is deposited on the probe 2 through the sample dispenser 6. The sample dispenser 6 is then withdrawn from the cuvette 1 and an electric current is passed through the cuvette 1, the current heating the cuvette to a desired temperature which is below the atomisation temperature but which is sufficient to evaporate the sample solvent. The actuator then withdraws the probe 2 from the cuvette to the second position as shown in FIG. 2. The cuvette 1 is then heated to a temperature sufficient to atomise the sample to be atomised by passing a greater electric current through it and when the cuvette 1 has reached the atomising temperature the actuator 3 moves the probe 2 into the first position as shown in FIG. 1 so that the sample on the probe is atomised by heat radiated from the walls of the cuvette.

This method of atomisation has a number of advantages. Since the cuvette 1 is at a steady temperature before the sample is inserted, the possibility of the sample being atomised by the hotter central portion of the cuvette, condensing on the cooler end portions, and then being re-atomised as the whole cuvette heats up is reduced; the speed of atomisation may be increased due to the lower thermal mass of the probe; by sampling onto the probe within the cuvette a standard autosampler can be used; and by using the cuvette to evaporate the sample solvent a second heat source is rendered unnecessary.

When analysing certain samples, such as body fluids, a carbonaceous mass may be formed on the probe after the drying step. In this case the temperature of the cuvette 1 is further increased to ash the sample before the probe is withdrawn from the cuvette. This second ashing temperature is, of course, below that required to atomise the sample. When analysing solid samples it is, of course, not necessary to perform the step of drying the sample and consequently in that case the probe may be withdrawn from the cuvette before any current is applied to the cuvette and only re-inserted when the cuvette has reached the atomisation temperature. Although drying of solid samples is not necessary, it may be necessary to ash some solid samples, in which case the temperature of the cuvette 1 is raised to the ashing temperature before the probe is withdrawn from the cuvette.

The described method of atomising the sample may be used in atomic absorption, atomic emission, and atomic fluoresence spectroscopy. The form of the cuvette 1 may have to be modified to enable the particular technique to be used. The cuvette shown in FIGS. 1 to 4 is suitable for atomic absorption or emission spectroscopy but for atomic fluorescence measurements of viewing path transverse to the illumination path, which is along the axis of the tube, must be provided. Such arrangements would be readily apparent to the worker skilled in the art.

FIGS. 5, 6 and 7 show the cuvette 1, probe 2, and actuator 3 mounted in and on a furnace for an atomic absorption spectrophotometer. The furnace comprises a body 10 having a hinged door 11. Within the furnace body 10 two contact jaws, one of which is shown at 12, grip each end of the cuvette 1. The jaws have electrical connection terminals, one of which is shown at 13, to which an electrical current source may be connected for passing a current through the cuvette. The contact jaw 12 comprises a fixed lower portion 14 and a pivoted upper portion 15 which can be pivoted by moving a member 16 into the body 10, horizontally to the left in the embodiment shown in FIG. 7. The actuator 3, which is in the form of a solenoid, is attached to the door 11 of the furnace by four screws 17 to 20 and the probe 2 passes through an aperture 21 in the door 11. A further aperture 22 is provided in the front of the door 11 through which the dosing tube 6 may be inserted to deposit a sample on the probe. Preferably the aperture 22 is closed when the cuvette is being heated so that the escape of protective gas is reduced. Since the cuvette 1 is normally made of carbon, it is necessary to prevent rapid oxidation when it is heated to the atomising temperatures, which may be in the region of 3000° C. Consequently it is customary to provide a flow of inert gas over and through the cuvette 1.

The door 11 is hinged along its bottom edge, being mounted between two fixed members 21 and 24 by a shaft 25, the ends of which are free to rotate in the fixed members 23 and 24. The opening and closing of the door 11 is performed by a rod 26 pivotally connected to a lug 27 on the door 11 and operated by a piston 28 in a cylinder. A quartz window 29 is set in both sides of the door 11 with the quartz windows being aligned with the longitudinal axis of the tubular body 1. The door 11 is normally kept closed and only opened to replace the cuvette when it has reached the end of its life.

FIG. 8 shows an atomic absorption spectrophotometer which comprises a radiation source 80, which may be, for example, a hollow cathode lamp, whose radiation is directed to pass through the cuvette 1 within the furnace body 10 via the quartz windows 29. The radiation then passes through a monochromator 81 and impinger on a detector 82. A control unit 83 is connected to the furnace to provide the appropriate voltages at and for the appropriate times for the cuvette and also to provide control signals for the solenoid actuator and for the flow of protective gas over the cuvette. Such controllers are well known in the art for providing the currents for drying, ashing and atomising the samples with one arrangement being described in German Pat. No. 2008295. The operation of the solenoid merely requires a signal which causes the probe to be withdrawn when the atomisation current is fed to the cuvette. The controller 83 may comprise the unit sold by Pye Unicam Limited as the PU9095 Video Furnace modified to give a further output to control the solenoid actuator.

The spectrophotometer shown in FIG. 8 may be a currently manufactured instrument such as the Pye Unicam SP9 or PU9000 series with the furnace door assembly modified to provide the facilities shown in and described with reference to FIGS. 5 to 7 together with the probe and actuator assembly and a cuvette having a probe entry slot.

Modifications may be made to the embodiments shown, for example, the cuvettes may be made from any suitable material, the furnace may be of different construction, the form of the cuvette may be modified to be suitable for use in atomic emission or atomic fluorescence spectroscopy, and the probe actuator may comprise a motor and cam arrangement or an arrangement similar to that shown in U.K. Patent Application No. 2088582A.

We claim:

1. A method of atomizing a sample for atomic spectroscopy comprising the steps of
   inserting a probe into a cuvette,
   separately depositing a sample onto said probe within said cuvette,
   heating said cuvette to a first temperature below an atomization temperature of said sample to dry said sample within said cuvette,
   withdrawing said probe and said sample from said cuvette after said sample is dried,
   thereafter heating said cuvette to a second temperature, said second temperature being at least equal to said atomization temperature of said sample,
   reinserting said probe and said sample back into said cuvette, and
   atomizing said sample in said cuvette at said second temperature.

2. A method according to claim 1, wherein said cuvette is heated to a third temperature to ash said sample between the steps of heating said cuvette to said first temperature and withdrawing said probe and said sample from said cuvette, said third temperature being less than said atomizing temperature.

3. A spectrophotometer having an electrothermal atomizer comprising
   a tubular body of electrically conductive material having a plurality of openings,
   first means for inserting a probe into said tubular body through one of said openings,
   second means for depositing a sample onto said probe within said tubular body through another of said openings, and
   third means for heating the interior of said tubular body, said third means passing an electric current through said tubular body to provide a first temperature for drying said sample,
   wherein said first means removes said probe and said sample after said sample is dried, and
   wherein said third means heats said interior of said tubular body to at least an atomizing temperature of said sample after said sample has been dried and removed from said tubular body,
   said first means reinserting said sample back into said tubular body at said atomizing temperature to atomize said sample.

4. A spectrophotometer according to claim 3, wherein said first means includes a solenoid.

5. A spectrophotometer according to claim 3 or 4, wherein said tubular body is a pyrolytic graphite body.

6. A spectrophotometer according to claim 5, wherein said probe is a pyrolytic graphite probe.

7. A spectrophotometer according to claim 3 or 4, wherein said probe is a pyrolytic graphite probe.

8. A spectrophotometer according to claim 3 or 4, wherein said third means heats said tubular body to a third temperature for ashing said sample, said third temperature being between said first temperature and said atomizing temperature.

* * * * *